United States Patent [19]

Ganz et al.

[11] 4,430,083
[45] Feb. 7, 1984

[54] INFUSION CATHETER

[75] Inventors: William Ganz, Los Angeles; Ronald J. Solar, Mission Viejo; Clement Lieber, Yorba Linda, all of Calif.

[73] Assignee: American Hospital Supply Corporation, Evanston, Ill.

[21] Appl. No.: 241,291

[22] Filed: Mar. 6, 1981

[51] Int. Cl.$^3$ .............................................. A61M 25/00
[52] U.S. Cl. .................................. 604/283; 128/772; 604/265
[58] Field of Search ................... 128/348, 772; 604/48, 604/57, 93, 115, 264, 272, 280, 265, 282, 283

[56] References Cited

U.S. PATENT DOCUMENTS

| | | | |
|---|---|---|---|
| 3,352,303 | 11/1967 | Delaney | 128/24 |
| 3,605,750 | 9/1971 | Sheridan | 128/348 |
| 3,618,613 | 11/1971 | Schulte | 128/348 |
| 3,631,848 | 1/1972 | Muller | 128/348 |
| 3,722,505 | 3/1973 | Kolin | 73/194 EM |
| 3,736,939 | 6/1973 | Taylor | 128/349 B |
| 3,757,768 | 9/1973 | Kline | 128/348 |
| 3,935,857 | 2/1976 | Co | 128/348 |
| 3,938,501 | 2/1976 | Erikson | 128/348 |
| 4,033,331 | 7/1977 | Guss et al. | 128/348 |
| 4,080,706 | 3/1978 | Heilman et al. | 128/772 |
| 4,117,836 | 10/1978 | Erikson | 128/348 |
| 4,169,464 | 10/1979 | Obrez | 128/348 |
| 4,184,497 | 1/1980 | Kolff et al. | 128/348 |
| 4,207,900 | 6/1980 | Patel et al. | 128/349 B |
| 4,381,008 | 4/1983 | Thomas et al. | 604/265 |

FOREIGN PATENT DOCUMENTS

| | | | |
|---|---|---|---|
| 2528273 | 9/1976 | Fed. Rep. of Germany | 604/265 |
| 462423 | 1/1914 | France | 604/264 |

OTHER PUBLICATIONS

"The Clinical Use of Fibrinolytic Agents" *The Amer. J. of Surgery* (NY, NY) Porter et al., p. 220.
"Selective Clot Lysis with Low-Dose Streptokinase" Dotter et al., *Radiology* 111:31–37 Apr. 1974, pp. 31–37.
"Arterial Thrombosis in a Patient with Chronic Thombocytopenia" Hirsh et al., *The Medical J of Australia*, 12-1969, p. 1304.
"Streptikonase in Acute Myocardial Infarction", *New Eng. J. of Med* 10/1979, vol. 301.
"Streptokinase Treatment of Deep Venous Thrombosis" Albrechtsson et al., Arch Surs–vol. 116, Jan 1981, pp. 33–37.
"USCI Positrol II & Nycore Cardiovascular Cathetcis" USCI Trade Catalog.
"Intracoronary Thrombolysis in Evolving Myocardial Infarction" Ganz et al. *Amer. Heart J.*, Jan. 1981, pp. 4–12.

*Primary Examiner*—C. Fred Rosenbaum
*Assistant Examiner*—T. J. Wallen
*Attorney, Agent, or Firm*—Gordon L. Peterson

[57] ABSTRACT

A catheter comprising an elongated flexible tube having an elongated passage extending axially through the tube between proximal and distal openings and a helically wound wire engaging the peripheral wall of the tube and providing a portion of the peripheral wall with an uneven contour. The tube includes a radiopaque marker at the distal end of the catheter. The radiopaque marker is molded from a biocompatible metal powder and a thermoplastic binder. The catheter is adapted for use with an angiography catheter, and it is configured to provide automatic orientation of the distal end portion of the catheter as such distal end portion emerges from the distal opening of the angiography catheter.

5 Claims, 14 Drawing Figures

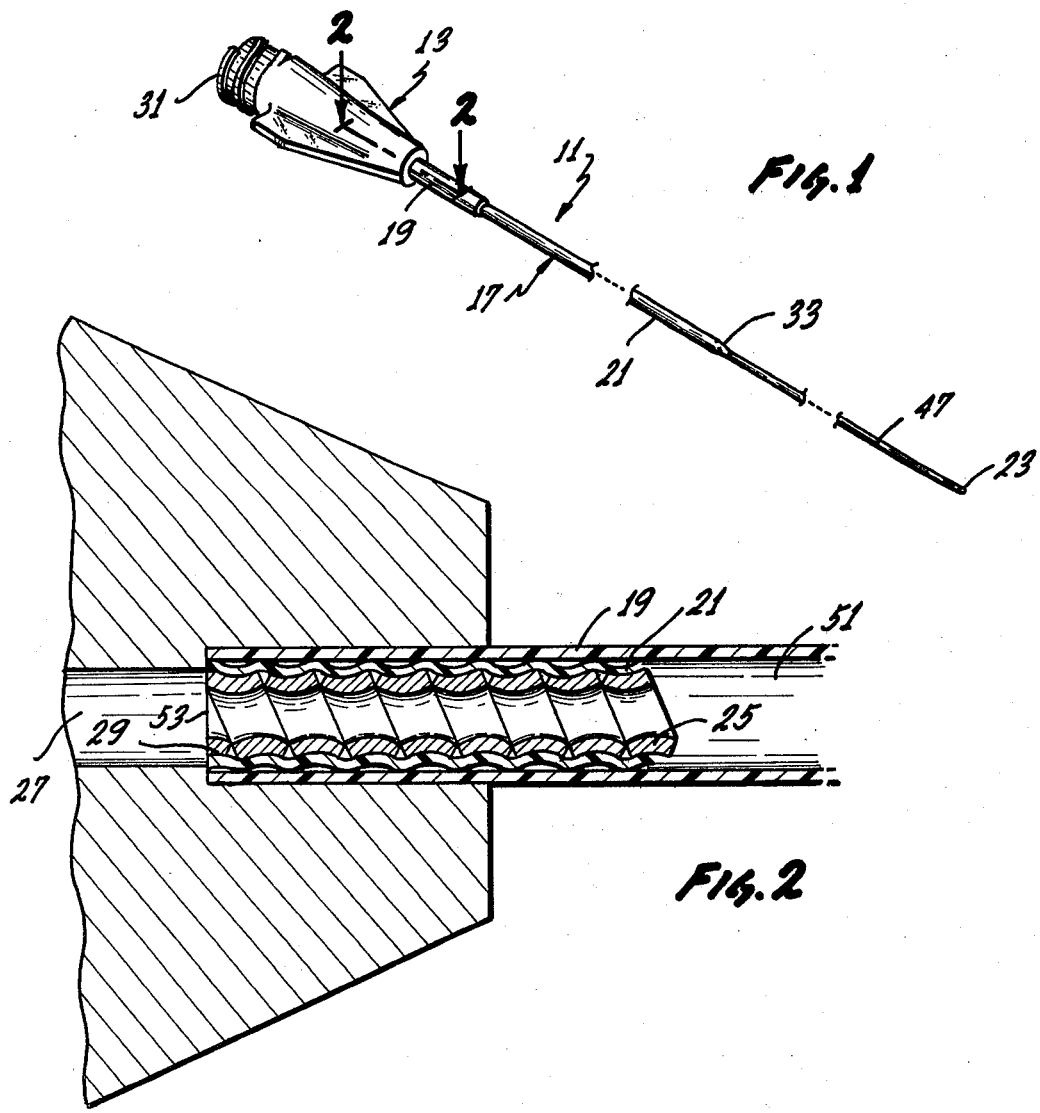
Fig. 1
Fig. 2
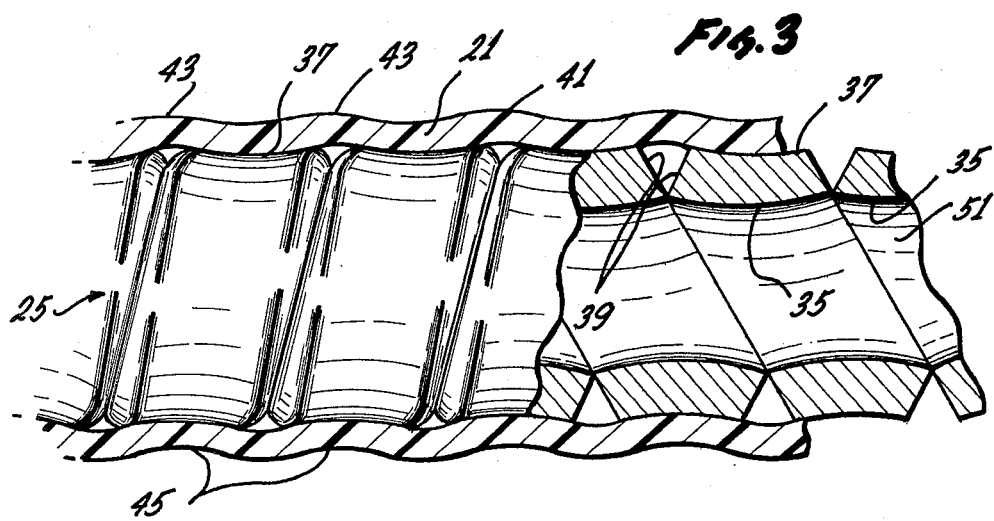
Fig. 3

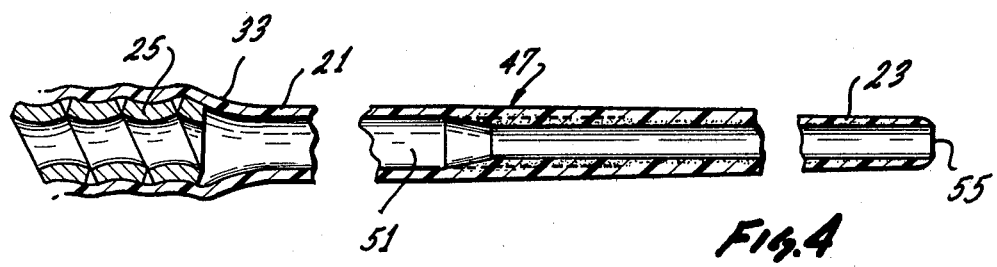
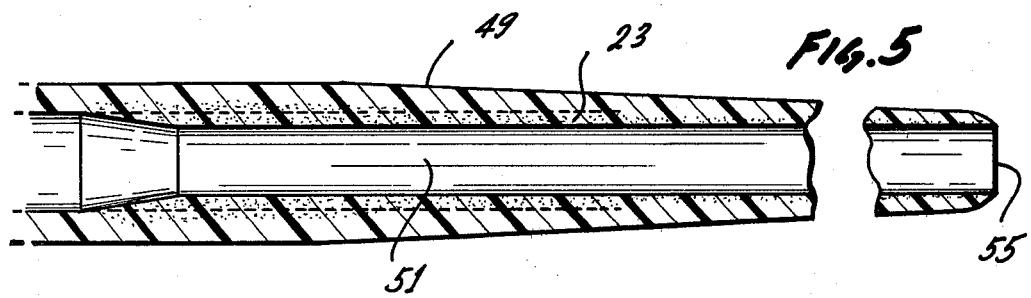
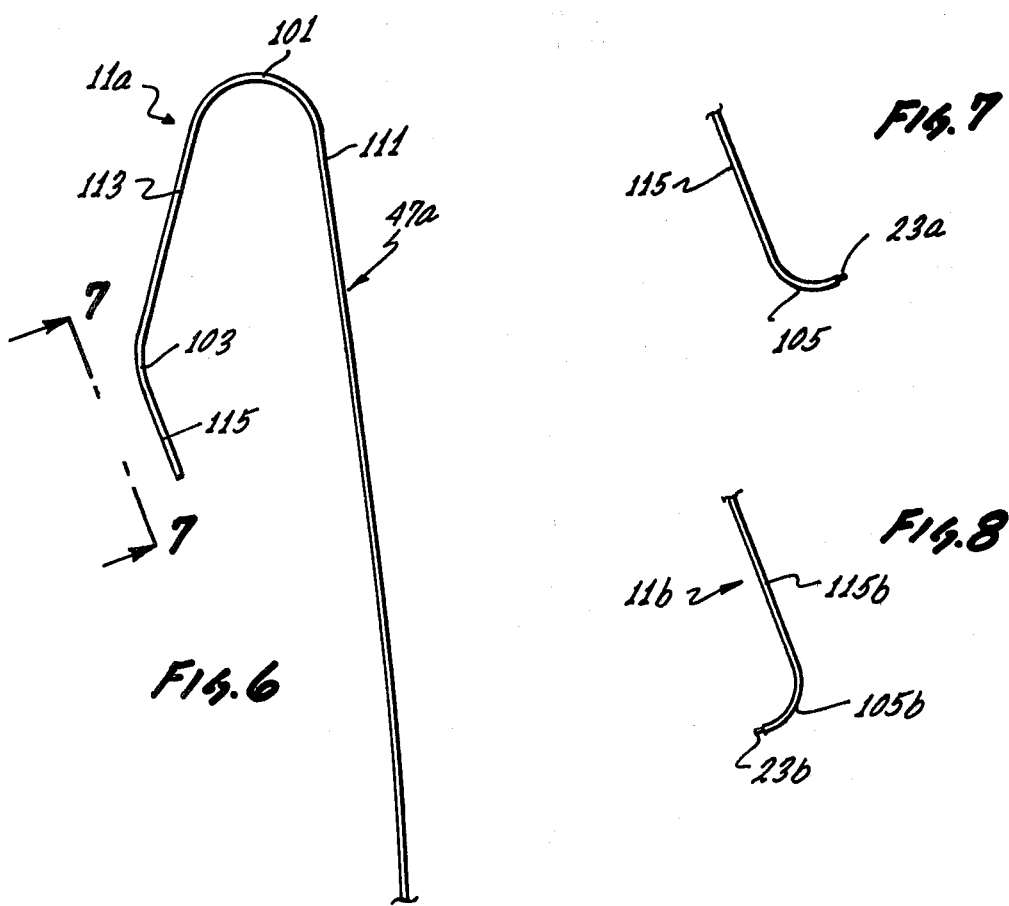

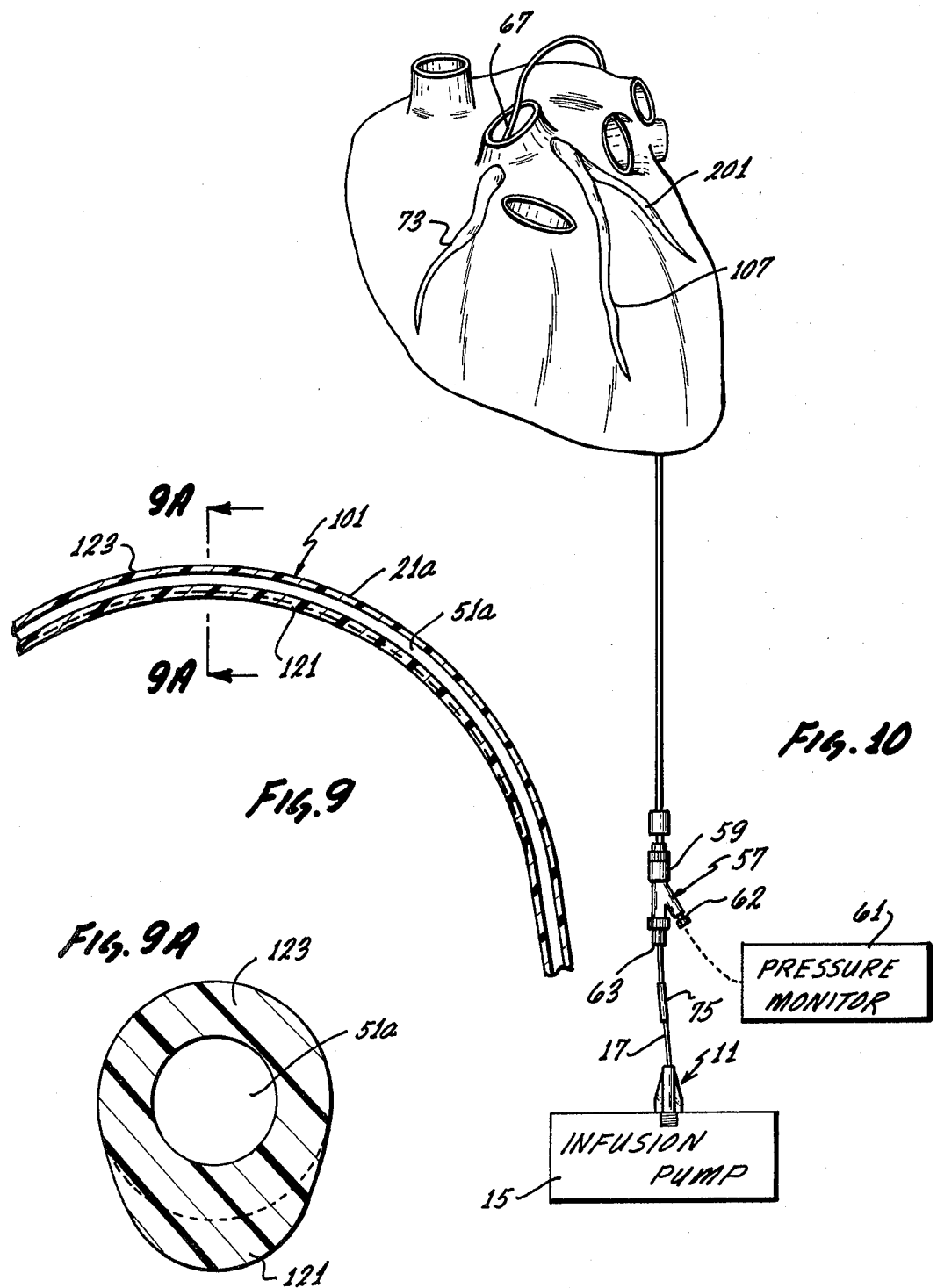

INFUSION CATHETER

BACKGROUND OF THE INVENTION

Acute myocardial infarction commonly occurs when a thrombus or clot occludes an artery of the heart. When this occurs, a thrombolytic agent, such as streptokinase is used to obtain lysis of the clot.

It is known to use thrombolytic agents systemically by administering them intravenously. However, such use of streptokinase involves a considerable risk of bleeding in patients.

Alternatively, the streptokinase or other thrombolytic agent can be infused locally into the general region of the thrombus. This can be accomplished, for example, by utilizing an angiography catheter in a procedure which first involves injecting dye to locate the clot, terminating the dye injection and then utilizing that same catheter to infuse the thrombolytic agent in the general region of the thrombus. Unfortunately, the angiography catheter has too large a diameter to enable its distal opening to be positioned in close proximity to distal clots. Accordingly, the action of the thrombolytic agent is not as localized as desired, and the agent may be shunted away from the clot by collateral vessels. Also, to determine if the clot is dissolved, infusion must be stopped and the dye flow started. This increases the time to obtain removal of the clot and, therefore, increases the likelihood of necrosis of the myocardium.

SUMMARY OF THE INVENTION

This invention solves these problems by utilizing a catheter which allows percutaneous administration of a thrombolytic agent directly to a clot in a coronary artery. Once acute myocardial infarction has been diagnosed and the location of the clot has been identified using an angiography catheter and conventional techniques, the catheter of this invention can be immediately advanced directly through the angiography catheter into the coronary arterial vasculature into close proximity to the clot. The thrombolytic agent can then be introduced through the catheter of this invention directly into the clot to minimize the likelihood of permanent damage to the heart muscle. This reduces the quantity of the thrombolytic agent infused and the risk of hemorrhaging is correspondingly reduced. Less time may be needed for this procedure, and the extent of necrosis of the myocardium may also be reduced.

The catheter may include an elongated, flexible tube having a peripheral wall, proximal and distal openings and an elongated passage extending generally axially through the tube between the openings. The flexible tube is supported by a helically wound wire which engages the peripheral wall of the tube. This wire has an axial cross-sectional dimension extending axially of the passage which is greater than the axial cross-sectional dimension of the wire which extends radially of the passage. This provides a catheter which has substantial column strength, relatively small outside cross-sectional dimensions and a relatively large cross-sectional area lumen.

It is believed that an uneven contour on the outer peripheral surface of the tube facilitates sliding movement of the tube in some environments. For example, in the presence of liquids or other flowable masses, an uneven contour on the peripheral surface may trap such liquids to provide lubricated movement of the catheter. Accordingly, this invention provides the outer peripheral surface of the tube with an uneven contour over at least a portion of the length of the tube. Although this can be accomplished in different ways, the helically wound wire can be formed, in the winding process, into a tubular configuration which has an irregular outer peripheral surface which deforms the outer peripheral surface of the tube. Preferably, the wire is helically wound into a series of tight, contiguous coils to provide the outer peripheral surface of the wire with an anticlastic curvature. The tube can advantageously include heat shrink tubing shrunk into tight engagement with the helically wound wire.

The wire-tube combination remains flexible. However, it is desirable to provide the tube with a distal end portion which is somewhat softer and more flexible to avoid any damage to the coronary artery. This can be accomplished, for example, by allowing the distal end portion of the tube to extend beyond the end of the helically wound wire so that the distal end portion is unsupported by the wire. Accordingly, the distal end portion of the tube is smooth and flexible. When in use within an angiography catheter, the proximal end of the distal end portion remains within the angiography catheter.

It is important to identify the location of the distal opening of the catheter, and for this purpose, a radiopaque marker is provided. Although other locations are possible, it is preferred to locate the radiopaque marker at the distal opening so that the distal opening can be accurately located when the catheter is in use.

Because the catheter is of very small cross-sectional area and because the distal end must be accurately located, a very small radiopaque marker having substantial radiopacity must be used. In addition, the radiopaque marker must be strongly secured to the catheter so that it will not become dislodged when in use. To accomplish these objectives, the present invention utilizes a radiopaque marker which includes a biocompatible metal powder having a specific gravity greater than 11 and a binder. For example, the biocompatible metal may include tantalum or gold, with tantalum being preferred. Of course, the biocompatible metal may include suitable metal alloys. A biocompatible metal having a specific gravity greater than 11 provides the necessary radiopacity for the small radiopaque marker.

The tube may include plastic tubing, such as heat shrinkable plastic tubing. To strongly secure the radiopaque marker to the tubing, the binder is preferably constructed of a material which can be fused to the material of the tubing. For example, elastomeric or thermoplastic materials can be used.

The distal end portion of the catheter can be configured to seek out a particular coronary artery. For example, it has been found that a straight catheter can be utilized to reach a clot in the right coronary artery, whereas passage-seeking bend sections should be used to facilitate insertion of the catheter into the left anterior descending coronary artery and the circumflex branch of the left coronary artery.

For catheters of this invention which have a passage-seeking bend section, it is important that this bend section emerge from the distal opening of the angiography catheter at the correct angular orientation. With this invention, orientation is automatically provided as the catheter is passed through the angiography catheter by providing the inner catheter with at least one orientation bend section in its distal end portion. This orientation bend section cooperates with a bend section of the angiography catheter to angularly orient the passage-seeking bend section. The angiography catheter may contain two bend sections, and in this case, the inner catheter can advantageously include two corresponding orientation bend sections cooperating with the two bend sections, respectively, of the angiography catheter. In a preferred configuration, the orientation bend sections of the inner catheter will roughly correspond in configuration and spacing to the bend sections of the angiography catheter so that the orientation bend sections are within the bend sections of the angiography catheter when the passage-seeking bend section is just outside the distal opening of the angiography catheter.

As described above, the outer catheter is the orienting member, and the inner catheter is the oriented member. However, the orienting feature of this invention are equally applicable when the inner catheter or other inner member is the orienting member and the outer catheter or other outer member is the oriented member. Thus, either the inner or outer member may orient the other and either, or both of these members may be catheters.

Although the configuration of the distal end portion of the catheter will vary depending upon the configuration of the outer catheter which is to be used, in one preferred construction, the orientation bend sections lie in the same plane, and the passage-seeking bend section lies in a plane transverse to the plane of the orientation bend sections. In one embodiment, the first orientation bend section has an included angle which is substantially greater than the included angle of the second orientation bend section.

Although the catheter is described as being for use with an angiography catheter in treating acute myocardial infarction, the catheter can be used for other purposes and in conjunction with other catheters.

The invention, together with further features and advantages thereof, may best be understood by reference to the following description taken in connection with the accompanying illustrative drawing.

BRIEF DESCRIPTION OF THE DRAWINGS

FIG. 1 is a perspective view of a catheter constructed in accordance with the teachings of this invention.

FIG. 2 is an enlarged, fragmentary sectional view taken generally along line 2—2 of FIG. 1.

FIG. 3 is an enlarged, fragmentary sectional view taken on an axial plane through the tubing of the catheter and showing portions of the helically wound spring in elevation.

FIG. 4 is an enlarged, fragmentary sectional view showing an end portion of the catheter.

FIG. 5 is an enlarged, fragmentary sectional view of a region of the distal end portion of the catheter.

FIG. 6 is a fragmentary plan view illustrating a catheter having an end portion of a different configuration.

FIG. 7 is a fragmentary side elevational view taken generally along line 7—7 of FIG. 6.

FIG. 8 is a fragmentary sectional view similar to FIG. 7 showing another configuration for the catheter.

FIG. 9 is an enlarged fragmentary sectional view illustrating one of the bend sections of the catheter of FIG. 6.

FIG. 9A is an enlarged sectional view taken generally along line 9A—9A of FIG. 9.

FIG. 10 is a diagrammatic illustration of an angiography catheter and the catheter of this invention being utilized to infuse a thrombolytic agent into the heart.

BRIEF DESCRIPTION OF THE PREFERRED EMBODIMENTS

Figure 11:
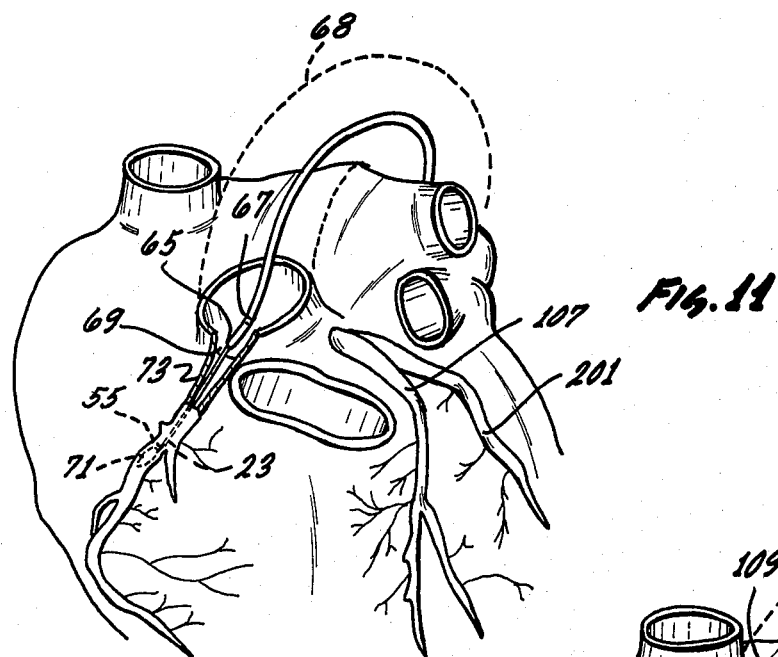
FIG. 11 shows the catheter of FIGS. 1–5 being utilized in association with an angiography catheter to infuse a thrombolytic agent directly onto a clot in the right coronary artery.

FIG. 1 shows a catheter 11 which generally includes a hub or connector 13 adapted for connection to an infusion pump 15 (FIG. 10) or other fluid handling device and a tube 17 coupled to the connector. The tube 17 includes a relatively short length of strain relief tubing 19, flexible tubing 21 which extends for substantially the full length of the tube 17, and a radiopaque marker 23 (FIG. 4). The catheter 11 also includes a helically wound wire 25 within the tubing 21.

The connector 13 is constructed of a rigid plastic material and has an axial bore 27 (FIG. 2), a counterbore 29 and a threaded section 31 to facilitate its attachment to the infusion pump 15 (FIG. 10). The strain relief tubing 19 is constructed of heat shrink plastic and is seated in the counterbore 29. The tubing may be attached to the connector 13 by adhesive or by direct fusion of the plastic materials of the tubing 19 and the connector 13. The strain relief tubing is stiffer than the tubing 21 and projects a short distance axially of the connector 13 to provide strain relief for the tubing 21.

The tubing 21 is long and flexible and, in the embodiment illustrated, it is constructed of heat shrink polyvinylchloride (PVC). The tubing 21 is fused directly to the plastic material of the strain relief tubing 19, although an adhesive could be utilized, if desired.

The helically wound wire 25 forms a tubular structure within the passage of the tubing 21, and the tubing is shrunk into tight engagement with the helically wound wire 25. The wire 25 is tightly wound with the adjacent coils being in contact with each other. The helically wound wire 25 extends from the proximal end of the tubing 21 to a location 33 (FIG. 1) spaced from the distal end of the tube. The wire may be constructed of metal or a suitable plastic.

As shown in FIG. 3, the wire 25 has an inner surface 35 and an outer surface 37. In the unwound condition, the surfaces 35 and 37 are planar and parallel. However, the wire is wound sufficiently tightly and is otherwise constructed and arranged so as to induce stresses to provide a transverse curvature known as anticlastic curvature in the outer surface 37 as shown in FIG. 3. In addition, the wire 25 has end faces 39 which are separated to form a gap, and this gap can be the result of the anticlastic curvature and/or the configuration of the end faces. The anticlastic curvature and the gaps provide the helically wound wire 25 with an irregular outer peripheral surface. When the tubing 21 is shrunk into tight contact with the outer surface 37 of the wire 25, the uneven contour of the outer surface 37 provided by the anticlastic curvature deforms the tubing 21. Accordingly, the tubing 21 has an outer peripheral surface 41 which is uneven and which contains a multiplicity of peaks 43 separated by valleys 45.

As shown in FIGS. 2 and 3, the wire 25 has an axial cross-sectional dimension which is substantially greater than the radial cross-sectional dimension of the wire. The aspect ratio is preferably at least 2-to-1, and in the embodiment illustrated, 3-to-1. This provides good column strength and an increased lumen diameter for the catheter 11.

The tube 17 extends beyond the location 33 (FIG. 3) at which the helically wound wire 25 terminates to define a distal end portion 47 which is unsupported by the wire 25 and is, therefore, more flexible than the portion of the tube which is supported by the wire. The distal end portion may be considered as being joined to a proximal portion of the catheter. In addition, the distal end portion 47 has a smooth outer peripheral surface as shown in FIG. 4. The tubing 21 necks down slightly at the location 33 to provide the distal end portion 47 with a reduced diameter. In the form shown in FIGS. 1-4, the distal end portion 47 is normally generally cylindrical, although it can be readily deformed due to its flexible nature.

The radiopaque marker 23 (FIGS. 4 and 5) includes a biocompatible metal powder having a specific gravity of greater than 11 and a binder. In the embodiment illustrated, the metal powder is tantalum and the binder is PVC. Although different ratios can be used, the tantalum and PVC may represent 75 percent and 25 percent, respectively, by weight of the marker 23.

Although different methods of construction can be employed, the marker 23 is preferably molded into a tubular section having an axial passage extending through it. The tubular section is placed within the outer end portion of the tubing 21 and they are fused together with heat and pressure to cause the plastic of the binder and the plastic of the tubing to become an integral mass, with the powdered tantalum dispersed therein. This results in the radiopaque marker 23 being soft and resiliently flexible. Preferably, this assembly process also provides a tapered outer surface 49 on the tubing 21 as shown in FIGS. 4 and 5.

The tube 17 has an elongated axial passage or lumen 51 extending between a proximal opening 53 and a distal opening 55. As shown in FIGS. 4 and 5, the radiopaque marker forms the very distal tip of the tube 17 and also defines the distal opening 55, and although this is preferred, other constructions can be utilized.

The tube 17 and the wire 25 are constructed in small diameters. By way of example and not by way of limitation, the region of the tubing 21 supported by the helically wound wire 25 may have an outside diameter of 0.033 inch and the inside diameter of the helically wound wire 25 may be 0.014 inch. The wire 25 may have an axial dimension of about 0.015 inch and a radial transverse dimension of about 0.005 inch. With this construction, the wall thickness of the tubing 21 may be about 0.0045 inch. The distal end portion may have a length of about 7.8 inches, and the radiopaque marker may have a length of approximately 0.200 inch.

Although the catheter 11 may be used for different purposes, it is particularly adapted for treating acute myocardial infarction. To accomplish this, an angiography catheter 57 (FIGS. 10 and 11) of conventional construction is utilized. Although various different kinds of angiography catheters may be used, the catheter 57 is a right coronary catheter of the Judkins type and it includes a body member 59 which can be coupled to a pressure monitor 61 through a port 62, a proximal opening 63, a distal opening 65, a lumen extending between the openings, and a bend section 67 adjacent the distal opening.

In use, the angiography catheter 57 is percutaneously inserted through an artery, such as the femoral artery, using conventional techniques to bring the distal end portion of the catheter through the aorta 68, with the distal opening 65 being at, or closely adjacent, the ostium 69. Using conventional angiography techniques, a clot or occlusion 71 can be located in the right coronary artery 73. The clot or occlusion may totally or only partially block the artery 73.

To accomplish this, the distal end portion of the catheter 11 is introduced through the proximal opening 63 of the angiography catheter 57 and into the lumen of the angiography catheter. Initial insertion of the catheter 11 is facilitated by a lead-in sleeve 75 slidably mounted on the tube 17. The catheter 11 is passed through the lumen of the angiography catheter 57 out the distal opening 65 through the ostium 69 and into the right coronary artery 73. The distal end portion 47 is long enough so that the location 33 remains within the angiography catheter. The location of the radiopaque marker 23 and, hence, the distal opening 55 can be closely monitored fluoroscopically. When the distal opening 65 is in close proximity to the clot 71 in the right coronary artery, a thrombolytic agent can be introduced through the catheter 11 utilizing the infusion pump 15. The thrombolytic agent may be, for example, streptokinase, urokinase or Thrombolysin. The pressure within the heart can be monitored through the angiography catheter 57 by the pressure monitor 61 while the infusion is taking place. At the direction of the physician, pressure monitoring can be terminated and a dye introduced through the port 62 to determine whether or not the artery 73 has been cleared of the clot 71. Infusion of the agent can continue until the clot is removed.

FIGS. 6 and 7 show a catheter 11a which is identical to the catheter 11 in all respects not shown or described herein. Portions of the catheter 11a corresponding to portions of the catheter 11 are designated by corresponding reference numerals followed by the letter "a."

Figure 12:
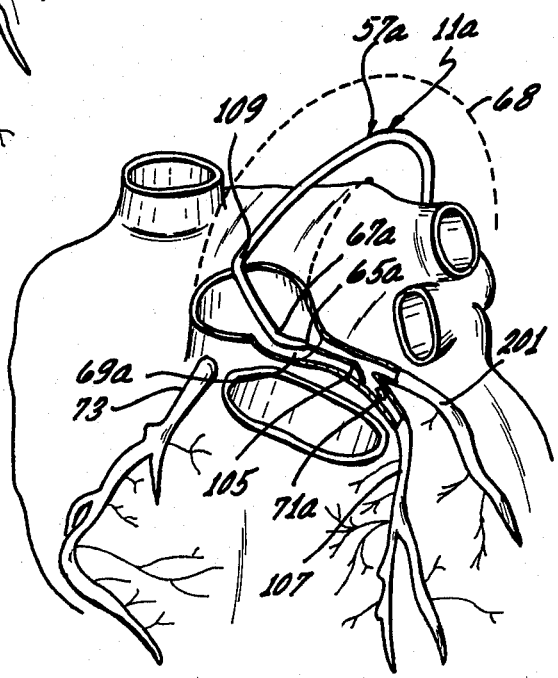
FIG. 12 is a view similar to FIG. 11 showing the catheter of FIGS. 6 and 7 being utilized to infuse a thrombolytic agent into a clot in the left anterior descending coronary artery.

The only difference between the catheters 11 and 11a is in the configuration of the distal end portions. Specifically, the distal end portion 47 is straight, whereas the distal end portion 47a has two resilient orientation bend sections 101 and 103 and a passage-seeking bend section 105 which is also resilient. The passage-seeking bend section 105 is configured to seek out the left anterior descending coronary artery 107 (FIG. 12). The orientation bend sections 101 and 103 automatically orient the passage-seeking bend section 105 when the catheter 11a is used within an angiography catheter, such as an angiography catheter 57a (FIG. 12) which is designed for exploring the left coronary arteries.

The catheter 57a is a left coronary catheter of the Judkins type and has bend sections 67a and 109 adjacent the distal opening 65a of the catheter 57a. Although the specific features of the catheter 11a are tailored to make that catheter compatible with a Judkins type left coronary catheter, other configurations for the catheter of this invention can be used to adapt the catheter for use with other outer catheters.

The bend sections 101 and 103 are preferably spaced a distance approximately equal to the spacing between the bend sections 109 and 67a, and the bend sections 101 and 103 are similar to the bend sections 109 and 67a, respectively, in that corresponding bend sections bend or curve in the same direction. The included angles formed by the bend sections 101 and 109 are less than the included angles formed by the bend sections 103 and 67a, respectively.

With reference to FIGS. 6 and 7, it can be seen that the bend section 105 lies in a plane which extends transverse to the plane of the bend section 103. In the embodiment of FIGS. 6 and 7, the bend sections 101 and 103 are in the same plane, although other arrangements can be used. In the specific form shown in FIGS. 6 and 7, the bend section 101 joins legs 111 and 113, and the bend section 103 joins the legs 113 and a leg 115. Each of the bend sections 101, 103 and 105 is a portion of a circle with the radius of the bend section 103 being the largest and the radius of the bend section 105 being the smallest. The bend section 105 is joined to the leg 115. The radiopaque marker 23a is at the distal end of the bend section 105.

The catheter 57a is used in the same manner as the catheter 57, except that the former has its distal opening 65a at the ostium 69a. The catheter 11a is used in the same manner as the catheter 11, except that the passage-seeking bend section 105 enters the left anterior descending coronary artery 107 to administer the thrombolytic agent to a clot 71a in that artery. In addition, the advancing of the catheter 11a through the catheter 57a brings about the necessary cooperation between the bend sections 109 and 67a with the orientation bend sections 101 and 103, respectively, to properly angularly orient the passage-seeking bend section 105 so that it will enter the artery 107. It is believed that orientation of the bend section 105 takes place as a result of orientation bend sections 101 and 103 resiliently seeking their natural or unstressed condition, and this they are allowed to do when they are within the associated bend sections 109 and 67a, respectively, of the catheter 57a. This rotates the bend section 105 into the correct position so that the bend section 105 is angularly oriented as it emerges from the distal opening 65. The bend section 105 can then be advanced the short distance between the ostium 67a and the beginning of the artery 107 so that it will enter the artery 107.

Figure 13:
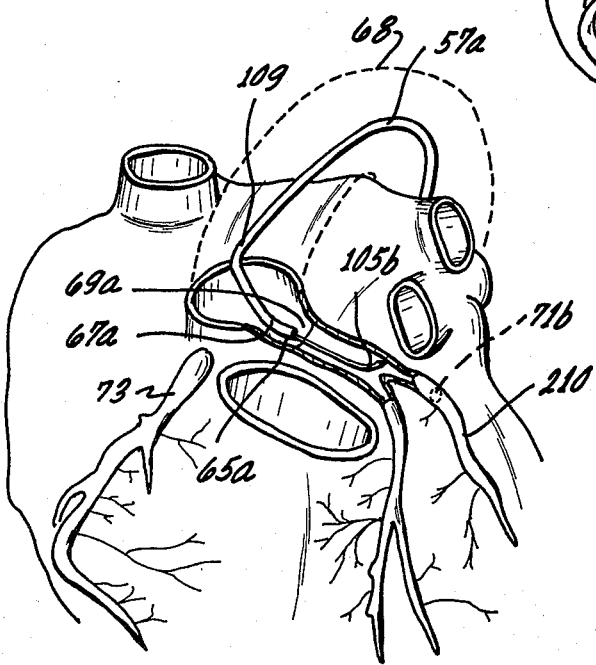
FIG. 13 is a view similar to FIG. 11 showing the catheter of FIG. 8 being utilized to infuse a thrombolytic agent directly onto a clot in the circumflex branch of the left coronary artery.

FIG. 8 shows a catheter 11b which is identical to the catheter 11a, except that the bend section 105b is displaced 180 degrees from the bend section 105. The catheter 11b can be used with the angiography catheter 57a as shown in FIG. 13 in the same manner as described above with reference to FIG. 12. In terms of the operation, the only difference is that the bend section 105b emerges from the distal opening 65a approximately 180 degrees displaced from the bend section 105. Accordingly, the passage-seeking bend section 105b tends to travel toward and enter the circumflex branch 201 of the left coronary artery so that it can be used to administer a thrombolytic agent to a clot 71b in the circumflex branch. In use, the catheter 57a would be advanced beyond the position shown in FIG. 13 to bring the distal end of the catheter closer to the clot 71b.

The bend sections of the catheters of FIGS. 6–8 are flexible and resilient, and a preferred form of construction is shown in FIGS. 9 and 9a. FIG. 9 shows a portion of the bend section 101 which is integrally formed by a region of the tubing 21a and has the lumen 51a therein. The bend section 101 has an inner concave region 121 and an outer convex region 123, with the peripheral wall of the tubing 21a being thicker at the inner concave region than the outer convex region. By causing the material of the tubing 21a to take a "permanent set", the thickened inner concave region 121 tends to resist outward bending of the tubing 21a. For example, if the tubing 21a is constructed of PVC, the tubing can be bent into the configuration shown in FIGS. 6 and 7 and additional PVC in a solvent applied to the inner concave region. The solvent is then driven off leaving the inner concave region 121 thicker than the outer convex region to thereby give the tubing a permanent set at the bend section 101. The other bend sections can be similarly constructed.

Although the invention has been described and illustrated with reference to a preferred embodiment which is particularly adapted for infusing a thrombolitic agent into the heart, it would be apparent that the apparatus and method can be equally advantageous for the infusion of other types of fluids into different areas of the vascular system. For example, the catheter of this invention can be used to infuse a thrombolitic agent into the lower limbs and thereby facilitate lower limb salvage. The catheter may also be of advantage in chemotherapy wherein various agents must necessarily be infused into specific areas of the vascular system.

It should also be understood that the infusion catheter can be used alone or in conjunction with interior or exterior guide means. In the latter case, the catheter can be moved either exteriorly of a guide wire or interiorly of a guide catheter to achieve its desired location.

These and other features and advantages, as well as modifications and substitutions, will be apparent to those having ordinary skill in this art, so that the scope of the invention should be ascertained only with reference to the following claims.

We claim:
1. A catheter comprising:
   an elongated flexible tube having a distal end, a peripheral wall, proximal and distal openings and an elongated passage extending generally axially through the tube between said openings;
   a helically wound wire engaging the peripheral wall of the tube, said helically wound wire including a plurality of turns and providing increased column strength, said tube with said helically wound wire therein being flexible;
   said wire having an inner surface, an outer surface, end faces, an axial cross-sectional dimension which extends axially of said passage between said end faces and a radial cross-sectional dimension which extends radially of said passage between said inner surface and said outer surface, said axial cross-sectional dimension being greater than said radial cross-sectional dimension; and
   said helically wound wire having an outer peripheral surface and being wound and configured so as to provide said outer peripheral surface with an anticlastic curvature, said tube being in tight engagement with the outer peripheral surface of said helically wound wire and being deformed thereby so as to provide the outer peripheral surface of the tube with an uneven contour over at least a portion of the length of the tube.

2. A catheter as defined in claim 1 wherein said tube includes heat shrink tubing shrunk into tight engagement with said helically wound wire.

3. A catheter as defined in claim 1 wherein said tube has a distal end portion which extends beyond the end of the helically wound wire whereby said distal end portion is unsupported by said helically wound wire and is more flexible than the portion of said tube which is supported by said helically wound wire and said tube includes radiopaque marker means at the distal end of said tube.

4. A catheter as defined in claim 1 including radiopaque marker means adjacent said distal end, said marker means including a biocompatible metal powder and a binder.

5. A catheter as defined in claim 3 or 4 wherein said distal end portion has at least one bend section therein spaced from said radiopaque marker means.

* * * * *